United States Patent
Chong et al.

(10) Patent No.: US 8,962,040 B2
(45) Date of Patent: Feb. 24, 2015

(54) VAPORIZED MEDICANTS AND METHODS OF USE

(71) Applicants: Alexander ChinHak Chong, St. Louis Park, MN (US); William Bartkowski, Edina, MN (US); Marshall Thompson, Camarillo, CA (US)

(72) Inventors: Alexander ChinHak Chong, St. Louis Park, MN (US); William Bartkowski, Edina, MN (US); Marshall Thompson, Camarillo, CA (US)

( * ) Notice: Subject to any disclaimer, the term of this patent is extended or adjusted under 35 U.S.C. 154(b) by 0 days.

(21) Appl. No.: 13/653,320

(22) Filed: Oct. 16, 2012

(65) Prior Publication Data

US 2013/0072577 A1    Mar. 21, 2013

Related U.S. Application Data

(63) Continuation-in-part of application No. 12/858,382, filed on Aug. 17, 2010, now Pat. No. 8,287,922.

(60) Provisional application No. 61/234,562, filed on Aug. 17, 2009.

(51) Int. Cl.
| | | |
|---|---|---|
| *A61K 36/00* | (2006.01) | |
| *A61K 36/34* | (2006.01) | |
| *A61K 47/10* | (2006.01) | |
| *A61K 9/00* | (2006.01) | |
| *A61K 47/26* | (2006.01) | |

(52) U.S. Cl.
CPC .............. *A61K 36/34* (2013.01); *A61K 47/10* (2013.01); *A61K 9/0078* (2013.01); *A61K 47/26* (2013.01); *Y10S 514/958* (2013.01)
USPC .......................................... 424/725; 514/958

(58) Field of Classification Search
None
See application file for complete search history.

(56) References Cited

U.S. PATENT DOCUMENTS

| | | | |
|---|---|---|---|
| 5,234,008 A | 8/1993 | Fagg | |
| 5,240,016 A | 8/1993 | Nichols et al. | |
| 5,486,362 A | 1/1996 | Kitchell et al. | |
| 6,513,524 B1 | 2/2003 | Storz | |
| 2004/0031495 A1 | 2/2004 | Steinberg | |
| 2006/0204598 A1 | 9/2006 | Thompson | |
| 2006/0239935 A1 * | 10/2006 | Bouyssou et al. | 424/46 |
| 2007/0280652 A1 | 12/2007 | Williams | |
| 2008/0060663 A1 | 3/2008 | Hamade et al. | |
| 2008/0166303 A1 | 7/2008 | Tamarkin et al. | |
| 2008/0173300 A1 | 7/2008 | Justman | |
| 2008/0241255 A1 | 10/2008 | Rose et al. | |
| 2008/0257367 A1 | 10/2008 | Paterno et al. | |
| 2009/0118331 A1 | 5/2009 | Crooks et al. | |
| 2010/0242974 A1 | 9/2010 | Pan | |

FOREIGN PATENT DOCUMENTS

| | | | |
|---|---|---|---|
| JP | 60009462 A * | 1/1985 | |
| JP | 01221313 A * | 9/1989 | |
| SG | 142127 A1 * | 5/2008 | |

OTHER PUBLICATIONS

Wikipedia_Lobelia, Last modified Feb. 28, 2012, Retrieved from the Internet: <http://en.wikipedia.org/wiki/Lobelia>.
International Search Report for PCT/US2010/45806 dated Sep. 29, 2010.
International Search Report for PCT/US2010/045804 dated Oct. 14, 2010.

* cited by examiner

*Primary Examiner* — Qiuwen Mi
(74) *Attorney, Agent, or Firm* — Cislo & Thomas, LLP

(57) ABSTRACT

A method and formulation for delivering an active compound in a vaporized state using low temperatures to vaporize the formulation. The formulation contains an inert non-reactive compound that lowers the heat of vaporization of the formulation, and the active compound. The formulation may optionally contain glycerin, alcohol, and/or water. Examples of inert non-reactive compounds that can sufficiently lower the heat of vaporization of the formulation include propylene glycol and polysorbate. The formulation can be vaporized using a hand-held low temperature vaporizer or atomizer.

8 Claims, No Drawings

VAPORIZED MEDICANTS AND METHODS OF USE

CROSS-REFERENCE TO RELATED APPLICATION

This patent application is a continuation-in-part of U.S. Utility patent application Ser. No. 12/858,382, filed Aug. 17, 2010 (now U.S. Pat. No. 8,287,922), which claims the benefit of U.S. Provisional Patent Application No. 61/234,562, filed Aug. 17, 2009, which applications are incorporated in their entirety here by this reference.

TECHNICAL FIELD

This invention relates to methods and formulations for vaporizing medicants and uses thereof.

BACKGROUND

When faced with a condition giving rise to bodily discomfort, such as a diseased state, disorder, ailment, normal bodily disruptions, and the like, most people turn to medication, such as drugs, supplements, herbs, and the like for immediate relief from the symptoms that arise from the underlying condition. There are certain legal and widely available over-the-counter (OTC) medications and supplements that have beneficial effects when used for a variety of common conditions. There are also certain controlled narcotics and pharmaceuticals prescribed by doctors for a variety of more serious conditions.

One of the most common routes of administration of these OTC and prescription drugs is oral administration. However, as with any oral delivery of medication, it must pass through the digestive tract. There are a number of disadvantages of oral administration. For example, because the drug has to pass through the digestive system, the onset of activation of the drug is slow. In addition, in the digestive tract the drug may be inactivated or destroyed, and therefore, lose its potency or efficacy. The drug itself can also cause problems in the digestive tract, or side effects, such as loss of appetite, diarrhea, acidity, and the like. Furthermore, patients may be reluctant or unable to swallow a pill.

Other routes of delivery exist, such as intradermal injections, patch applications, inhalations, and the like. Each of these has its own advantages and disadvantages. Therefore, there is still room for improving routes of administration of drugs.

For example, there are varieties of medicants which are safer, more effective, and more efficient with respect to efficacy if their ingestion is via inhalation of a vapor containing the medicant or its active ingredient rather than by gastrointestinal, intravenous or intramuscular delivery. However, most vaporization methodologies for inhalation are done at relatively high temperatures and, as a result, present risks or hurdles to either the efficacy of the medicant or the well-being of the user.

Certain medicants are intended to affect the brain or the brain's actions or activities but, given the accepted method of ingestion—gastrointestinal, intravenous, or intramuscular—these medicants can also have a variety of discomforting side effects due to the nature of ingestion or injection. These include, but are not limited to gastro-intestinal complications, digestive disorders, high blood pressure, and/or headaches.

Additionally, certain methods to vaporize and deliver these medicants have drawbacks as well, specifically those that vaporize the medicant itself, changing the molecular or chemical structure of the medicant or those that vaporize an excipient at a high temperature, once again changing the molecular or chemical structure of the excipient and raising the risk of changing the chemical structure of the medicant when it interacts with the vaporized excipient.

In order to ensure that the medicant is delivered intact via inhalation it is critical that the method of vaporization does not change the chemical or fundamental molecular structure of the medicant or excipient. Therefore, there is still a need for improving the routes of administration of drugs. In particular, there is still a need for improving inhalers that can meter exact dosages without destroying the active ingredient.

SUMMARY

The invention of the present application discloses a method and formulation that can generate a vapor state of a medicant or active ingredient metered at precise dosages without destroying or damaging the medicant or active ingredient, or the excipient solution. In particular, a formulation has been devised in which the solution can be vaporized at a low, focused temperature that ensures vaporization of the excipient and not of the active ingredient; allowing for the inhalation of a specific, accurate serving or dose of the active ingredient via an inert excipient. Specifically, excipient with a low vaporization temperature may be combined with an active ingredient that may have a higher vaporization temperature. In such a combination, the vaporizing excipient effectively acts as a carrier for the active ingredient. When the combination is heated to a temperature sufficient to vaporize the excipient, the excipient vapor carries molecules of the active ingredient along with it. Thus, the active ingredient is effectively "vaporized" at a temperature that is usually considerably lower than needed to vaporize the active ingredient alone.

In one embodiment, a method for medicant delivery is provided comprising: providing a medicant solution suitable for vaporization in a compact handheld device; providing the compact handheld device; vaporizing the medicant at a low temperature upon activation by a user such that an effective serving of the medicant is provided to the user.

In another embodiment, a medicant solution is provided for use in a vaporization delivery mechanism, the solution comprising: water; alcohol; an inert non-reactive compound; and an active ingredient. In some embodiments, the water and alcohol are optional. In some embodiments, the medicant solution may include glycerin (vegetable or otherwise) and/or flavoring. The medicant solution is formulated such that it can be vaporized at a low temperature in a sufficient quantity to provide an effective serving of the active ingredient to a user.

The method and solution is designed to be used with a delivery device such as that described in U.S. patent application Ser. Nos. 13/453,939; 13/044,355; and 61/470,460 which applications are incorporated in their entirety here by this reference.

Accordingly, the method and formulation can be used to vaporize a variety of medicants, preferably, medicants directed primarily toward neuro-activity. For example, these medicants include, but are not limited to, caffeine; alkaloids, such as yohimbine and codeine; hormones, such as melatonin and serotonin-classified; antihistamines, such as diphenhydramine; opioids, such as morphine and oxycodone; nootropics, such as piracetam; and amino acids, such as gamma-Aminobutyric acid (GABA).

These medicants can be further classified by their consumer/patient use on a PRN (as needed) basis. These classes include 1) sleep aids—melatonin and GABA; 2) motion sickness antidote—diphenhydramine; 3) energy and alertness aids—caffeine; 4) analgesics—morphine, codeine and oxycodone; and, 5) sexual aids—yohimbine.

Other features and advantages of the present invention will become apparent from the following detailed description. It should be understood, however, that the detailed description and the specific examples, while indicating the preferred embodiments of the present invention, are given by way of illustration only, since various changes and modifications within the spirit and scope of the present invention will become apparent to those skilled in the art from this detailed description.

DETAILED DESCRIPTION OF THE INVENTION

The detailed description set forth below is intended as a description of presently-preferred embodiments of the invention and is not intended to represent the only forms in which the present invention may be constructed or utilized. The description sets forth the functions and the sequence of steps for constructing and operating the invention. It is to be understood, however, that the same or equivalent functions and sequences may be accomplished by different embodiments that are also intended to be encompassed within the spirit and scope of the invention.

In order to fully understand the manner in which the above-recited details and other advantages and objects according to the invention are obtained, a more detailed description of the invention will be rendered by reference to specific embodiments thereof.

In one embodiment, a medicant solution is provided comprising an excipient and an active ingredient, in which the excipient can be vaporized at low temperatures relative to temperatures required by typical vaporizers. In another embodiment, a medicant delivery method is provided comprising providing a medicant solution that can be vaporized at low temperatures, and providing a device for vaporization of the medicant solution such that a user can absorb the vaporized solution via activation of the vaporization device to deliver an effective serving of medicant to a user.

While an effective serving, effective dose, or therapeutically effective amount of a medicant may vary depending upon the particular physiology of the user, for example, the user's weight or body make-up, as used herein, the phrases effective serving, effective dose, and therapeutically effective amount (used interchangeably) means an amount sufficient such that the user experiences the intended positive effects experienced when the medicant is delivered through other known methods. In one aspect of this embodiment the effective serving can be delivered in as little as one activation of the delivery device by the user, and in other aspects the effective serving may be delivered through multiple activations of the delivery device by the user over 1, 2, 3, 4, 5, 6, 7, 8, 9, 10 or more minutes of use in a manner similar to the use associated with using a portable, handheld aerosol breath freshener.

Alternatively, the effective serving can be delivered over a specified number of activations of the delivery device by the user. Further, the number of activations can occur over a specified time period. For example, delivery of an effective serving can be provided with 1, 2, 3, 4, 5, 6, 7, 8, 9, 10, 11, 12, 13, 14, 15, 16, 17, 18, 19, or 20 activations. For example, the effective does may be delivered in 1-20 activations, 5-15 activations, 12-20, activations, 12-18 activations or about 15 activations, any of which can occur in a 1, 2, 3, 4, 5, 6, 7, 8, 9, 10, or 20 minute period. Some embodiments will be formulated and/or configured such that the effective does is delivered as quickly as possible, and other embodiments can be formulated and/or configured such that the effective does is delivered in about the same time and manner as if one were using a portable, handheld aerosol breath freshener.

In various embodiments, a single serving may be delivered in less than 50 activations, about 1-50 activations, about 1-20 activations, about 5-15 activations or about 8-10 activations. The single serving may include greater than about 0.5 mg, from about 0.5 mg to about 100 mg, from about 0.5 mg to about 50 mg, from about 0.5 mg to about 20 mg, from about 0.5 to about 10 mg, from about 5 mg to about 10 mg, or about 5 mg of the medicant solution.

The formulation of the medicant solution comprises an active ingredient and an excipient capable of vaporizing at low temperatures. When the medicant solution is heated, the excipient vaporizes at a relatively low temperature, carrying the active ingredient with it. Even though the active ingredient may have a higher vaporization temperature, the excipient vapor transports molecules of the active ingredient, delivering the active ingredient to the user at a low temperature.

The excipient may comprise one or more of an inert non-reactive compound, e.g., propylene glycol, polysorbate, and/or glycerin, such that the medicant solution can be vaporized at low temperatures for activation by a user. In some embodiments, the excipient may further comprise water and/or alcohol. In some embodiments, water is present at a concentration of about 0.01% to about 30% of the excipient. Preferably, water is present at about 0.01% to about 20%. More preferably, water is present at about 2% to about 18%. More preferably, water is present at about 5% to about 15%. Most preferably, water is present at about 10% of the excipient.

In some embodiments, alcohol is present at a concentration of about 0.01% to about 30% of the excipient. Preferably, alcohol is present at about 0.01% to about 20% of the excipient. More preferably, alcohol is present at about 2% to about 18%. More preferably, alcohol is present at about 5% to about 15%. Most preferably, alcohol is present at about 10% of the excipient.

Once the other components of the excipient have been added, the remainder of the solution may be made up of propylene glycol, polysorbate, and/or glycerin. In some embodiments, propylene glycol, polysorbate, and/or glycerin can be used alone or in any combination thereof as the excipient.

In some embodiments, propylene glycol may be added to the excipient. Propylene glycol may be present at concentrations of at least 70% of the excipient. Preferably, propylene glycol is present at at least about 85% of the excipient. More preferably, propylene glycol can make up the entire excipient to which the active ingredient may be added.

In some embodiments, polysorbate may be added to the excipient, such as polysorbate 20, 40, 60, 65, or 80. Polysorbate may be present at concentrations of at least 70% of the excipient. Preferably, polysorbate is present at at least about 85% of the excipient. More preferably, polysorbate can make up the entire excipient to which the active ingredient may be added. Without being bound by theory, it is believed that polysorbate provides a more robust vapor upon vaporization, reduces the heat of vaporization, and produces smaller vapor molecules, thereby achieving deeper lung penetration upon inhalation.

In another aspect of the invention, the excipient may comprise glycerin. In the preferred embodiment, glycerin may be present at concentrations of at least about 70% of the excipient. More preferably, glycerin may be present at at least about 85% of the excipient. More preferably, glycerin can make up the entire composition of the excipient to which the active ingredient may be added. Without being limited by theory, it is believed that the addition of glycerin provides a more robust vapor upon vaporization of the product.

In another aspect of this invention, the medicant solution further comprises flavoring.

The medicant solution is formulated such that an effective serving of the active ingredient can be delivered to a user in a specified time period when the medicant solution is vaporized and inhaled by the user. In one aspect of this embodiment the effective serving can be delivered over a specified time period when the solution is vaporized without the addition of heat.

Depending on the form of the active ingredient the medicant solution may be prepared by combining a tincture of an active ingredient with the excipient. In some embodiments, the medicant solution may be prepared by contacting the active ingredient with the excipient. In other words, the medicant solution is prepared by extracting the active ingredient from its source (for example, herbs, plants, roots, etc.) with the excipient. The final concentration of the active ingredient may be controlled by the time, temperature, and pressure at which the source is in contact with the excipient.

For example, to promote the leaching or extracting of the active ingredient from its source, various methods may be employed to contact the source with the excipient, including maximizing the surface area of the source. In one embodiment, the source is formed in the shape of a mesh screen through which the excipient is passed. While the excipient is passed through the source, the active ingredient is extracted from the source into the excipient. In other configurations, the source is formed to provide the maximum surface area for contact with the excipient yet still allow flow of the excipient through the source and into a vaporization device. Examples of other configurations for use in maximizing the surface area of the source for contact with the excipient include spirally winding the source, converting the source into pellets, converting the source into powder, or encapsulating the source in a porous, filter-like material, which will allow the excipient to flow through the source-encapsulate allowing the active ingredient to leach into the excipient from its source. Leaching and/or extracting may also be promoted through modifying the temperature of the excipient or the pressure under which the excipient is contacted with the source.

In some embodiments the excipient and the medicant source are contacted immediately prior to vaporization. In other embodiments the excipient and medicant source can be contacted over an extended period of time prior to vaporization. For example, the medicant source can be provided immersed in the excipient such that the excipient has been in contact with the medicant source for an extended period of time prior to vaporization. In such examples, the leaching or extraction of the active ingredient can be promoted by varying the conditions or other parameters during contact of the excipient with the medicant source. The medicant source can be removed from the formed medicant solution prior to providing the medicant solution to the end consumer for inclusion in a device for vaporization, or immediately prior to vaporization by draining the medicant solution from the medicant source.

The medicant solution is then vaporized by activation of a vaporization or delivery device by the user. Examples of vaporizers (particularly, hand-held low temperature vaporizer) or delivery devices that may be used to vaporize the medicant solution are disclosed in U.S. patent application Ser. Nos. 13/453,939; 13/044,355; 61/470,460, incorporated herein by reference. Other devices may be used, which include atomizers or other vaporizers known in the art or combinations thereof. Vaporization or atomization can be performed with or without the addition of heat to the solution.

For example, the solution to be vaporized can first be atomized providing for ease of vaporization without the addition of heat. In one aspect a low temperature vaporizer is provided. Low temperature means temperatures of the heating element of a vaporizer that is lower than traditional temperatures used. For example, traditional temperatures rely on heating elements that reach 300 degrees Celsius (C.) or higher. Therefore, low temperatures mean temperatures less than 250 degrees C. Preferably, low temperatures mean temperatures from approximately 100 degrees C. to approximately 250 degrees C. Preferably, low temperatures may be from approximately 180 degrees C. to approximately 250 degrees C. More preferably, low temperatures may be from approximately 180 degrees C. to approximately 225 degrees C. Even more preferably, low temperatures may be from approximately 180 degrees C. to approximately 200 degrees C.

These low temperatures also refer to the heat of vaporization of the medicant solution, where the heat of vaporization means the temperature at which the medicant solution vaporizes from a liquid state to a gaseous state. Therefore, the heat of vaporization for the medicant solution is from approximately 100 degrees C. to approximately 250 degrees C. Preferably, the heat of vaporization for the medicant solution is from 180 degrees C. to approximately 250 degrees C. More preferably, the heat of vaporization for the medicant solution is from approximately 180 degrees C. to approximately 225 degrees C. Even more preferably, low temperatures may be from approximately 180 degrees C. to approximately 200 degrees C. In some embodiments, an excipient with a lower heat of vaporization may be used, including but not limited to polysorbates. In such embodiments, low temperatures for vaporization may be preferably from approximately 90 degrees C. to approximately 200 degrees C., and more preferably from approximately 100 degrees C. to approximately 160 degrees C., and even more preferably, from approximately 110 degrees C. to approximately 140 degrees C.

In another embodiment, a device for implementing the medicant delivery methods set forth herein is provided comprising a shell, a mouthpiece, an air inlet provided on the external wall of the shell, a cell, an electronic circuit board, a normal pressure cavity, a sensor, an atomizer, a solution reservoir, a medicant reservoir, a solution stream passage, a negative pressure cavity provided in the sensor, an atomization cavity arranged in the atomizer, and an aerosol passage, wherein the solution reservoir is in contact with the medicant reservoir and the atomizer, and the air inlet, normal pressure cavity, atomizer, aerosol passage, gas vent and mouthpiece are interconnected.

In another embodiment, a device for implementing the medicant delivery methods set forth herein is provided comprising a shell, a mouthpiece, an air inlet provided on the external wall of the shell, a cell, an electronic circuit board, a normal pressure cavity, a sensor, an atomizer, a solution reservoir, a solution stream passage, a negative pressure cavity provided in the sensor, an atomization cavity arranged in the atomizer, and an aerosol passage, wherein the solution reservoir is in contact with the atomizer, and the air inlet, normal pressure cavity, atomizer, aerosol passage, gas vent and mouthpiece are interconnected. The solution reservoir may be configured to retain a medicant solution and medicant, or medicant solution that has previous been contacted with medicant.

In some embodiments the device is provided in the configuration of a cigar or cigarette. In other embodiments the device is provided in other configurations such that the device can be readily distinguished from a cigar or cigarette.

In some embodiments, the delivery device is a hand-held, personal portable device that is disposable. Moreover, in some embodiments the method of vaporization uses low temperatures to vaporize the medicant solution.

In another embodiment a disposable cartridge is provided comprising a medicant solution or medicant (or active ingredient) and an excipient as set forth herein. The cartridge can include one or more servings of medicant as set forth herein. In one aspect of this embodiment the cartridge can include between about 5-50 servings, between about 5-25 servings, between about 10-25 servings, between about 10-50 servings, between about 10-20 servings of medicant.

Ingestion via vapor inhalation provides effects within 30 to 90 seconds. The quick, efficient method of inhalation ingestion provides for lower doses and significantly minimizes the risk of over dosing and its attendant complications, as the effects are almost immediately felt. This reduces the tendency to take more medication before the effects have set on as in the case of orally ingested drugs that are absorbed through the digestive tract. Accordingly, the invention of the present application provides users with an easy-to-use, convenient medicant product.

EXAMPLES

Examples of medicants or active ingredients that can be used with the present invention include but are not limited to, caffeine; alkaloids, such as yohimbine and codeine; hormones, such as melatonin and serotonin-classified; antihistamines, such as diphenhydramine; opioids, such as morphine and oxycodone; nootropics, such as piracetam; amino acids, such as gamma-Aminibutyric acid (GABA); and appetite suppressants, such as green tea and hoodia.

Caffeine is an alkaloid, a bitter substance found in coffee, tea, soft drinks, chocolate, kola nuts, and certain medicines. It has many effects on the body's metabolism, including stimulating the central nervous system. This makes the consumer more alert and provides a boost of energy. Accordingly, caffeine may be used as the medicant in the invention of the present application.

Diphenhydramine is a first generation antihistamine mainly used to treat allergies and available in over the counter, non-prescriptive medications like Benadryl. Like most other first generation antihistamines, the drug also has a powerful hypnotic effect, and for this reason is often used as a non-prescription sleep aid. Diphenhydramine is thought to block the re-uptake of histamine neurotransmitters, thereby causing histamine to build up in the spaces called synapses that are present between nerve cells. This leads to sedative effects. Diphenhydramine works both centrally within the brain as well as in peripheral nerve cells in other parts of the body. It possesses other effects and can counter nausea due to motion sickness.

Among the traditional methods for ingesting Diphenhydramine as a sleep aid is by mouth in various and readily available digestible compounds. It would be more effective, quicker acting and less likely to cause gastro-intestinal distress or discomfort if Diphenhydramine were more quickly transported to the brain through the cardio-pulmonary system by ingesting and inhaling a vaporized product containing Diphenhydramine. A fast-acting Diphenhydramine may be particularly useful for relieving motion sickness in progress, or as a sleep aid taken at or after bedtime. Accordingly, Diphenhydramine may be used as the medicant in the invention of the present application.

Melatonin is a naturally occurring compound, a hormone, found in animals, plants, and microbes. In animals, melatonin is made by the pineal gland, a small gland in the brain. Very small amounts of it are found in foods such as meats, grains, fruits, and vegetables. It can be purchased as a dietary supplement.

Circulating levels of melatonin vary in a daily cycle, thereby regulating the circadian rhythms of several biological functions, including controlling the sleep wake cycles. Many biological effects of melatonin are produced through activation of melatonin receptors, while others are due to its role as a pervasive and powerful antioxidant, with a particular role in the protection of nuclear and mitochondrial DNA.

Today, Melatonin is used for a variety of purposes, but most often used for human sleep enhancement by regulating the sleep-wake cycle by causing drowsiness and lowering body temperature and affecting the central nervous system.

Among the traditional methods or ingesting Melatonin is by mouth in various and readily available digestible compounds. When used as a sleep aid, Melatonin is typically taken 30-60 minutes prior to bedtime, to allow the Melatonin time to dissolve in the stomach and absorb into the blood stream to take effect. It would be more effective, quicker acting and less likely to cause gastro-intestinal distress or discomfort if Melatonin were more quickly transported to the brain through the cardio-pulmonary system by ingesting and inhaling a vaporized product containing Melatonin. A quick-acting Melatonin would be particularly helpful as a sleep aid when taken at or after bedtime. Accordingly, Melatonin may be used as the medicant in the present application.

GABA is traditionally known as an inhibitory neurotransmitter involved in regulating neuronal communications through GABA receptors. GABA is naturally occurring in the human body. Supplementing a diet with GABA may have various benefits. Accordingly, GABA may be used as the medicant in the present application.

Morphine is regarded as the benchmark of analgesics used to relieve severe or agonizing pain and suffering. Morphine is the most abundant alkaloid found in opium. Like other opioids, e.g. Morphine (OxyContin, Percocet, Percodan), hydromorphone (Dilaudid, Palladone), and diacetylmorphine (heroin), morphine acts directly on the central nervous system (CNS) to relieve pain. Among the traditional methods or ingesting Morphine is by intravenous injection, traveling through the blood stream to the central nervous system. Morphine has a high potential for addiction; tolerance and psychological dependence develop rapidly. It would be more effective, quicker acting and less likely to cause gastro-intestinal distress or side effects such as itching, nausea, vomiting, drowsiness, dry mouth, miosis, orthostatic hypotension, urinary retention, depression and constipation if Morphine was more quickly transported to the brain through the cardio-pulmonary system by ingesting and inhaling a vaporized product containing Morphine. Accordingly, Morphine may be used as a medicant in the invention of the present application.

Codeine is an opiate analgesic drug that is used to relieve moderate to severe pain. Like morphine it is an alkaloid found in opium. Like other opiates, codeine acts directly on the central nervous system (CNS) to relieve pain. Codeine has a high potential for addiction; tolerance and psychological dependence develop rapidly. It would be more effective, quicker acting and less likely to cause side effects if codeine was more quickly transported to the brain through the cardio-pulmonary system by ingesting and inhaling a vaporized product containing codeine. Accordingly, codeine may be used as a medicant in the invention of the present application.

Oxycodone is an opioid analgesic medication synthesized from poppy-derived thebaine. It was developed in 1916 in Germany, as one of several new semi-synthetic opioids in an attempt to improve on the existing opioids, morphine and codeine. Oxycodone oral medications are generally prescribed for the relief of moderate to severe pain. Currently it is formulated as single ingredient products or compounded products. Some common examples of compounding are oxycodone with acetaminophen/paracetamol or NSAIDs such as ibuprofen. The formulations are available as generics but are also made under various brand names.

Among the traditional methods or ingesting Oxycodone is by mouth in various and readily available digestible compounds. It would be more effective, quicker acting and less likely to cause gastro-intestinal distress or side effects such as itching, nausea, vomiting, drowsiness, dry mouth, miosis, orthostatic hypotension, urinary retention, depression and constipation if Oxycodone was more quickly transported to the brain through the cardio-pulmonary system by ingesting and inhaling a vaporized product containing Oxycodone. Accordingly, Oxycodone may be a medicant used in the invention of the present application.

When used for pain, inhaling an active ingredient, which is rapidly effective, may minimize a user from taking additional doses while waiting for pain relief. Such rapid effects may lead to lower dosing and less tendency to overmedicate, which may lead to less chance of addiction, and less complications from overmedication.

Yohimbe is the principal alkaloid of the bark of a West Indian evergreen tree. It is used as a supplement to arouse sexual excitement, for erectile dysfunction (ED), sexual problems caused by medications for depression called selective-serotonin reuptake inhibitors (SSRIs), and general sexual problems in both men and women. It is also used for athletic performance, weight loss, exhaustion, chest pain, high blood pressure, low blood pressure that occurs when standing up, diabetic nerve pain, and for depression along with certain other medications. Yohimbe contains a chemical called yohimbine which can increase blood flow and nerve impulses to the penis or vagina. It also helps counteract the sexual side effects of certain medications used for depression. Yohimbe may be a medicant used in the invention of the present application.

Appetite suppressants exist naturally in certain plants. For example, green tea and the hoodia plant are believed to contain active ingredients that can suppress appetite. Numerous other plants and chemical compounds are also believed to have appetite suppressant properties. However, may not be practical to consume enough of these plant substances or extracts, such as green tea or hoodia, through the digestive system to feel the full effects. In addition, a rapidly-acting appetite suppressant may be beneficial in helping a user counteract sudden urges to eat. Accordingly, green tea, hoodia, and other appetite suppressant substances may be a medicant used in the invention of the present application, including with the extraction or leaching methods described herein.

Numerous other medicants can be used with the present invention. As such, the foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method for delivering medicants through inhalation, comprising:

a. acquiring a medicant solution suitable for vaporization at a low temperature, the medicant solution, comprising:
   i. an inert non-reactive compound, and
   ii. hoodia; and b. vaporizing the medicant solution at the low temperature such that an effective serving of the hoodia is provided to the user for inhalation, wherein the low temperature is from approximately 90 degrees C. to approximately 250 degrees C.

2. The method of claim 1, wherein the step of vaporizing the medic solution comprises using a low temperature vaporizer.

3. The method of claim 1, wherein the medicant solution further comprises approximately 0.01% to approximately 30% of water.

4. The method of claim 1, wherein the medicant solution further comprises approximately 0.01% to approximately 30% of alcohol.

5. The method of claim 1, wherein the inert non-reactive compound comprises polysorbate.

6. The method of claim 1, wherein the low temperature is from approximately 90 degrees C. to approximately 200 degrees C.

7. The method of claim 1, wherein the low temperature is from approximately 100 degrees C. to approximately 160 degrees C.

8. The method of claim 1, wherein the low temperature is from approximately 110 degrees C. to approximately 140 degrees C.

* * * * *